(12) United States Patent
Higazi

(10) Patent No.: US 6,759,042 B2
(45) Date of Patent: Jul. 6, 2004

(54) USE OF CROSS-LINKED, COVALENTLY BOUND UROKINASE PLASMINOGEN ACTIVATOR (SCUPA)-UROKINASE PLASMINOGEN ACTIVATOR RECEPTOR (SUPAR) COMPLEX AS A FIBRINOLYTIC AGENT

(75) Inventor: Abd. Al-Roof Higazi, Shimshon (IL)

(73) Assignee: Thrombotech LTD, Nazareth Illit (IL)

( * ) Notice: Subject to any disclaimer, the term of this patent is extended or adjusted under 35 U.S.C. 154(b) by 0 days.

(21) Appl. No.: 09/902,392

(22) Filed: Jul. 10, 2001

(65) Prior Publication Data

US 2001/0046495 A1 Nov. 29, 2001

Related U.S. Application Data

(63) Continuation-in-part of application No. 09/325,917, filed on Jun. 4, 1999.

(51) Int. Cl.[7] .................. A61K 39/395; A61K 39/40; A61K 39/42; A61K 38/00; C07K 2/00
(52) U.S. Cl. .................. 424/130.1; 424/134.1; 530/300; 530/350; 530/385; 530/386; 530/381; 530/382; 530/387.1
(58) Field of Search .................. 424/130.1, 134.1; 530/300, 350, 385, 386, 387.1, 380, 381, 382

(56) References Cited

U.S. PATENT DOCUMENTS

| 4,996,005 A | 2/1991 | Isukada et al. | 424/94.2 |
|---|---|---|---|
| 5,004,609 A | 4/1991 | Hayashi et al. | 424/94.3 |
| 5,055,295 A | 10/1991 | Welzel et al. | 424/94.2 |
| 5,626,841 A | 5/1997 | Gurewich | 424/94.63 |

FOREIGN PATENT DOCUMENTS

WO    WO 98/25641    *  6/1998

OTHER PUBLICATIONS

Higazi et al. Soluble Human Urokinase Receptor is Composed of Two Active Units. The Journal of Biological Chemistry 272(8): 5348–5353, Feb. 21, 1997.*
Higazi et al. Interaction of Single–Chain Urokinase With Its Receptor Induces the Appearance and Disappearance of Binding Epitopes Within the Resultant Complex for Other Cell Surface Proteins. Blood 88(2):542–551, Jul. 15, 1996.*
Marder VJ et al. e.g. N. Eng. J. Med. 1988; 318: 1512–1520.
Higazi et al., J. Biol. Chem. 1995, 270: 17375–17380.
Shliom et al., J. Biol. Chem. 2000, 275: 24304–24312.
Bdeir et al., Blood 2000, 96: 1820–1826.
The Gusto Angiographic Investigations N. Eng. J. Med 1993, 329: 1615: 1622.
Cannon CP et al., J. Am. Coll. Cardiol. 1994, 24: 1602–1610.
Zarich S. W. et al., J. Am. Coll. Cardiol. 1995, 26: 374–379.
Higazi et al., Blood 1998, 92: 2075–2083.

* cited by examiner

*Primary Examiner*—Alana M. Harris
(74) *Attorney, Agent, or Firm*—Rashida A. Karmali

(57) ABSTRACT

The present invention relates to the cross-linked scuPA/suPAR complex and/or tcuPA/suPAR cross-linked complex, the process of preparation of the covalently bound single compound having fibrinolytic activity and use of the cross-linked scuPA/suPAR or tcuPA/suPAR complex in the prevention and/or treatment of thrombolytic disorders. The invention further relates to combination compositions and/or therapy regimens, comprising the cross-linked scuPA/suPAR complex or tcuPA/suPAR and one or more currently used plasminogen activators to achieve improved therapeutic efficacy and/or reduce side effects.

11 Claims, 2 Drawing Sheets

USE OF CROSS-LINKED, COVALENTLY BOUND UROKINASE PLASMINOGEN ACTIVATOR (SCUPA)-UROKINASE PLASMINOGEN ACTIVATOR RECEPTOR (SUPAR) COMPLEX AS A FIBRINOLYTIC AGENT

CROSS-REFERENCE TO RELATED APPLICATIONS

This Application is a Continuation-in-Part of co-pending application Ser. No. 09/325,917, filed Jun. 4, 1999, and of co-pending application Serial No. unassigned, entering the natural stage filing in the United States on Oct. 5, 2001 from PCT/IL00/00208, both of which are hereby incorporated by reference specifically for disclosure on medical uses of non-cross-linked scuPA/suPAR and tcuPA in thromboembolic disorders.

FIELD OF THE INVENTION

The present invention relates to a process for preparing, and novel chemical complexes comprising the single chain unit of the urokinase type plasminogen activator ("scuPA") and, at least one unit of the soluble urokinase plasminogen activator receptor ("suPAR"), and use of the resulting scuPA/suPAR cross-linked complex as a fibrinolytic agent in the thromboembolic disorders. The invention is also directed to use of pharmaceutical compositions in prevention and/or treatment of thromoembolic disorders.

BACKGROUND TO THE INVENTION

Urokinase type plasminogen activator (uPA), widely used in the treatment of thromoembolic diseases, is biologically synthesized as a proehzyme comprising of a single-chain (scuPA). Limited proteolysis of scuPA results in the formation of two chains in the urokinase plasminogen activator (tcuPA), which is considered to be the active form of the enzyme.

An important regulator of uPA is the plasminogen activator inhibitor-1 (PAI-1), which interacts with tcuPA to form an inactive complex. The binding of tcuPA to the receptor uPAR only slightly reduces the susceptibility of tcuPA to the inhibitory effect of PAI-1.

In U.S. Pat. No. 4,996,005 by M. Tsukada et al, it was demonstrated that the combination of single-chain pro-urokinase and plasminogen enhanced the fibrinolytic activity of the single-chain pro-urokinase without causing systemic fibrinolysis. Typical examples of the single chain pro-urokinase used included those with a molecular weight of 50,000 to 55,000 having a single-chain peptide bond structure. And, plasminogen included sources from human or animal serum, plasma, ascites fluid, placenta extract or placenta tissue extract.

U.S. Pat. No. 5,004,609 by S. Hayashi et al., describes a complex of urokinase with a urokinase inhibitor having a molecular weight of 97,5000+3,000 and a method for producing the complex having the ability to dissolve thrombus.

U.S. Pat. No. 5,626,841 by V. Gurewich et al., describes a method of adjunctive therapy to inhibit reocclusion in a patient after thrombolytic treatment by administering to the patient a bolus of pro-urokinase after completion of a thrombolytic treatment and once every 1 to 10 days after the period of risk of occlusion.

Pro-urokinase has also been used in clinical trials for therapeutic thrombolysis in patients with myocardial infarction, pulmonary embolism or deep vein thrombosis.

U.S. Pat. No. 5,055,295 by Welzel et al. However, urokinase has a short half-life in blood and lacks noticeable affinity for fibrin. Therefore, its therapeutic use requires bolus-infusion administration in substantial doses which may lead to complications. See, Marder VJ et al. e.g. *N. Eng. J. Med.* 1988, 318:1512–1520. More effective thrombolysis has been attempted by a generation of plasminogen activator preparations using uPA conjugated with fibrinogen. See Maksimenko Av et al., e.g. Am NY Acad Sci 1990, 613:479–482.

Similarly, in co-pending application, U.S. application Ser. No. 09/325,917 by A. A. Higazi, a combination of a single chain urokinase type plasminogen activator and a soluble urokinase plasminogen activator receptor, for example, the native nature, non-cross-linked scuPA/suPAR complex under physiological conditions was described to be useful as a pharmaceutical composition for prevention and/or treatment of thromboembolic disorders. This composition was described to have improved fibrinolytic activity in the presence of human IgG or at least one human IgG-derived peptide in physiological conditions.

An additional co-pending application (Serial No. unassigned) by A. A. Higazi, describes the two chain urokinase composition (tcuPA) having a fibrinolytic activity when combined with suPAR (tcuPA/suPAR) under physiological conditions.

However, the binding of scuPA to suPAR is reversible and interruption of this binding leads to the loss of activity of the native, non-cross-linking scuPA/suPAR complex. J. Biol. Chem 1995, 270: 17375–17380. Moreover, the role of urokinase (scuPA) and its receptor (suPAR) in fibrinolysis may depend on the vascular location, the physical properties of the clot and its impact on tissue function, and physiological factors contributing to low affinity of suPAR to form dimmers or oligomers that bind scuPA. J.B.C. 2000, 275:24304–24312. The present invention is directed to achieve optimal, cross-linked and/or covalent binding of scuPA to suPAR and to maximize the activity of urokinase in the presence of the chemically prepared single compound, e.g., the cross-linked and/or covalent scuPA/suPAR complex. This is achieved by covalent cross-linked binding of scuPA to suPAR in phosphate buffered saline at 4° C. in the presence of sulfosuccinimidyl, instead of relying on the binding to take place under physiological and sometimes not easy to control conditions. The resulting chemical compound has novel properties, for example, it cannot undergo dissociation while at the same time, retains the activity of the corresponding native enzyme-receptor complex, for example, the cross-linked and/or covalent scu/PA/suPAR complex.

SUMMARY OF THE INVENTION

The present invention relates to the preparation and use of cross-linked and/or covalently bound single compounds having fibrinolytic activity for example, the scuPA/suPAR complex, comprising of chemically bound single chain urokinase type plasminogen activator (scuPA) and one or more molecules of soluble urokinase plasminogen activator receptors (suPAR).

More specifically, these compounds are useful in the prevention and/or treatment of thromboembolic disorders associated with formation of fibrin clots, for example, myocardial infarctions, celebro-vascular events, pulmonary embolism, peripheral vascular disease, deep vein thrombosis, coronary artery disease, hypercholesterolemia, hypertension, ischemic vascular disease, diabetes, hemoglobinopathies, or myeloproliferative disorders such as thrombocythemia and polycythemia.

The present invention also provides novel processes for the synthesis of cross-linked, covalent complexes of scuPA and suPAR in molar or excess of suPAR concentrations in the presence of sulfosuccinimidyl suborate at specific experimental conditions. The present invention also provides novel processes for the synthesis of cross-linked, covalent complexes of tcuPA/suPAR complex in equimolar or molar excess of suPAR.

Also contemplated by the present invention are methods of dissolving clots in mammals, such methods comprising administering to the mammal a pharmaceutical composition comprising non-cross-linked and/or covalently bound scuPA/suPAR, in an amount therapeutically effective to dissolve the clots, in combination with a physiological buffer.

Also contemplated by the present invention are methods of dissolving clots in mammals, such methods comprising administering to the mammal a pharmaceutical composition comprising non-cross-linked and/or covalently bound scuPA/suPAR, or tcuPA/suPAR in an amount therapeutically effective to dissolve the clots, in combination with a physiological buffer and an effective amount of human IgG.

Pharmaceutical kits for the treatment of thromboembolic disorders in a mammal comprise a sterile container of a pharmaceutical composition comprising cross-linked and/or covalently bound active scuPA/scPAR, or tcuPA/suPAR in an amount therapeutically effective to dissolve clots, in combination with a physiological buffer, and, if desired, mixtures of these, and other activators of plasminogen, comprising streptokinase, rt-PA or alteplase, rt-PA derivatives (such as reteplase, lanoteplase and TNK-rt-PA), platelet glycoprotein IIb-IIIa receptor inhibitors, plasminogen streptokinase complex (APSC) or anistreplase, tcu-PA or urokinase, recombinant scuPA (pro-uPA or prourokinase) and streptokinase and derivatives.

In yet another embodiment, the present invention pertains to processes for stabilizing the cross-linked, covalently bound scuPA/suPAR compound, comprising subjecting the scuPA/suPAR protein, to lyophilization, and then reconstituted in an amount therapeutically effective to prevent and/or treat thromboembolic disorders in a mammal.

Additionally, the present invention is directed to pharmaceutical kits for the treatment of thromboembolic disorders in a mammal, the kits comprising a sterile container of scuPA/suPAR, in lyophilized form, in an amount therapeutically effective to treat thromboembolic disorders, and at least one sterile container of a reconstitution liquid. The foregoing kits may further include, if desired, other fibrinolytic agents such as native non-cross-linked scuPA/suPAR or tcuPA/suPAR complex in an amount therapeutically effective to treat thromboembolic disorders.

BRIEF DESCRIPTION OF THE FIGURES

The advantages and features of the present invention will become readily apparent after reading the following detailed description and referencing the drawings, which are.

DETAILED DESCRIPTION OF THE INVENTION

Figure 1:
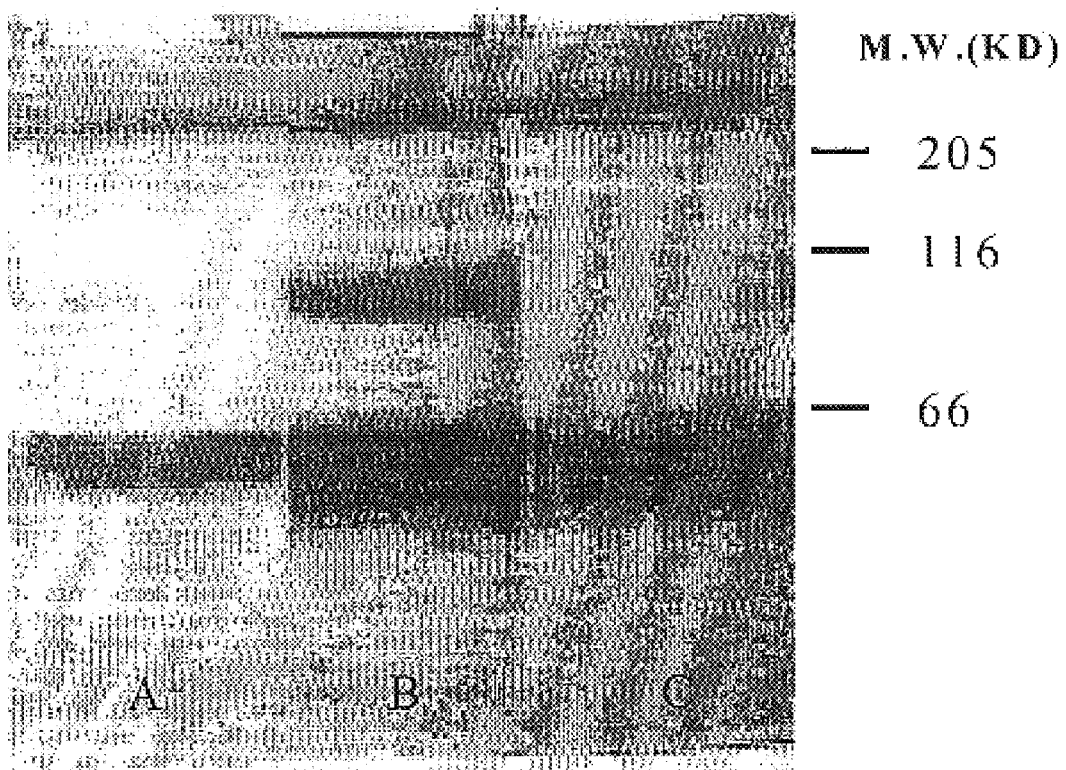
FIG. 1 is a diagram of an SDS-PAGE analysis of the scuPA bound to suPAR, showing the formation of a stable cross-linked and/or covalent scuPA-suPAR complex. Lane A shows scuPA alone. Lane B shows scuPA-suPAR complex. It shows the appearance of a higher molecular weight band that corresponds to the SDS-stable scuPA-suPAR complex. Lane C shows suPAR alone.

In accordance with the present invention, cross-linked and/or covalently bound scuPA/suPAR may be prepared chemically by combining one portion of scuPA with one or more portions of suPAR. Also, in accordance with the present invention, cross-linked and/or covalently bound scuPA/suPAR may be stabilized by subjecting it to lyophilization. The present invention further provides pharmaceutical compositions and kits that may be used in the prevention and/or treatment of thromboembolic disorders and provides a new approach aimed at increasing the efficacy of thrombolytic therapy using a mixture or combination of the cross-linked and/or covalently bound scuPA/suPAR complex of the present invention and other plasminogen activators with complementary mechanisms of action and different pharmacokinetic profiles from the compositions of the present invention.

CURRENTLY USED THROMBOLYTIC AGENTS

Thrombolytic agents that are either approved or under clinical investigation in patients with acute myocardial infarction include streptokinase, rt-PA or alteplase, rt-PA derivatives (such as reteplase, lanoteplase and TNK-rt-PA), anisolylated plasminogen streptokinase complex (APSC) or anistreplase, tcu-PA or urokinase, recombinant scuPA (pro-uPA or prourokinase) and streptokinase and derivatives.

Thrombolytic therapy is given to more than 750,000 patients per year worldwide, while at least three times that number could potentially benefit from this treatment.

The role of endogenous single chain urokinase type plasminogen activator (scuPA) and its receptor suPAR in fibrinolysis remains unclear although it was found that scuPA contributes to endogenous fibrinolysis in the pulmonary vasculature to the same extent that tPA does in the model. Blood 2000, 96: 1820–1826. Binding of endogenous scuPA to it's receptor promoted fibrinolytic activity in vivo and its activity may be linked to the physical properties of fibrin clots (such as size, age and cellular composition) as well as heterogeneity in endothelial cell function.

However, the binding of purified scuPA to suPAR and the activation of scuPA by the scuPA/suPAR formed, is reversible. Importantly, any interruption in the binding of the scuPA to suPAR leads to loss of action of scuPA. J. Biol. Chem 1995, 270: 1735–17380. This has been a major drawback in the application of scuPA as fibrinolytic agent.

Thus, although some success has been achieved in increasing the amount of scuPA/suPAR obtained, means for stabilizing this scuPA/suPAR, and minimizing its conversion to scuPA and scuPAR were needed. See co-pending U.S. application Ser. No. 09/325,917, the contents of which are incorporated by reference in its entirety, herein.

The present invention achieves this important end by providing a process to prepare a cross-linked and/or covalently bonded scuPA/suPAR single chemical compound. The new process comprises of chemical cross-linking of the scuPA/suPAR complex at equimolar concentrations of scuPA and suPAR or at higher (n) concentrations of scuPAR, in the presence of sulfosuccinimidyl and experimental conditions described below in detail. The chemically modified equimolar scuPA/suPAR complex or scuPA/n (SuPAR) complexes are covalently cross-linked and cannot undergo dissociation. The enzymatic activity of the cross-linked and/or complex compounds of the present invention are comparable to those of the unmodified native ones as described below in detail.

In another embodiment of the present invention, an excess of suPAR over scuPA or tcuPA in varying proportions, was found to increase the stability and/or activity of the resulting complexes formed, by the chemical bonding procedure of the present invention. These same complexes had been unstable and were undetectable by previous methods. J. Biol. Chem. 2000, 275: 24304–24312. Therefore, in the present invention, the chemical cross-linking and/or covalent binding of the complexes prepared using a molar excess of suPAR over scuPA or tcuPA leads to the development of novel complexes with a higher molecular weight and greater activity and potency than those obtained using equimolar concentrations and/or native non-cross-linked enzymes.

A preferred embodiment of the present invention comprises a cross-linked and/or scuPA/suPAR single chemical compound complex made from one molecule of scuPA and one molecule of suPAR, and exhibiting greater fibrinolytic activity than native non-cross-linked forms.

A more preferred embodiment of the present invention comprises a cross-linked scuPA/suPAR single chemical compound complex or tcuPA/suPAR made from one molecule of scuPA or tcuPA and two or more molecules of suPAR, and exhibits greater fibrinolytic activity than native non-cross-linked forms.

Clinical treatment of thrombosis has consisted mainly of administering thrombolytic agents intravenously or locally by catheter. Urokinase plasminogen activator is usually administered as the recombinant urokinase or single chain form scuPA, which forms a two chain urokinase tcuPA. t-PA and scu-PA have been shown in vitro and in animal models to be fibrin specific, that is, they selectively activate fibrin-bound plasminogen while leaving systemic plasminogen mainly unaffected.

Thrombolytic therapy with scu-PA, however, suffers significant shortcomings. The therapeutic doses of this plasminogen activator has been found to be high leading to a loss of fibrin-specificity and some systemic fibrinolytic activity, as evidenced by a drop in plasma fibrinogen levels upon dosage. As a result, thrombolytic therapy with scuPA is often complicated by hemorrhaging. Some attempts have been made to improve thrombolytic activity of scu-PA since enhancement of scuPA activity permits lowering the dose of scuPA and may result in less side effects.

The work described herein shows an improved method for enhancing the activity of scuPA by use of the chemically cross-linked, covalently bound scuPA/suPAR compounds which have been found to enhance activity of scuPA and therefore to lower the dose of scuPA and its side effects.

The present invention also suggests an improved thrombolytic therapy approach by increasing the thrombolytic activities of the combination regimen t-PA and scuPA in the presence of cross-linked, covalent scuPA/suPAR complexes of the present invention. This synergism is based on different mechanisms of action of the two plasminogen activators, for example, t-PA binds strongly to fibrin thus forming a complex with the plasminogen bound to the fibrin clot. ScuPA does not bind significantly to fibrin-clots in plasma. Its selectivity for fibrin-bound plasminogen results from a conformational change in plasminogen upon binding to fibrin which renders it more sensitive to activation by scuPA. In other words, t-PA and scuPA seem to activate different species of plasminogens bound to the fibrin clot.

Therefore, the present invention provides a combination of t-PA, scuPA and cross-linked, covalent scuPA/suPAR, to achieve improvement in thrombolytic activity while permitting lowering the dose of scuPA and thus lowering the likelihood of side effects.

The combination of scuPA/suPAR and any of the other thrombolytic agents, including tcu-PA, scuPA and IgG, streptokinase, acylated plasminogen-streptokinase activator complex, mixtures of these, and other activators of plasminogen is also within the scope of this invention.

The fibrinolytic activity of the non-cross-linked scuPA/suPAR complex was greater than that of tcuPA when a plasma clot was used. The present invention provides a cross-linked, covalently bound scuPA/suPAR complex also having a greater fibrinolytic activity than tcuPA.

The present invention also provides a pharmaceutical composition comprising cross-linked, covalently bound scuPA/suPAR complex in combination with an effective amount of IgG.

Clinical trials have demonstrated that during combined thrombolytic therapy of acute myocardial infarction, reocclusion is determined more by systemic hemostatic factors than by residual injury of the infarct related artery. Combined administration of tissue and urokinase-type plasminogen activators for patients with acute myocardial infarction has shown significant efficacy with low complication rates. The combined thrombolytic activity achieves a similar degree of angiographic patency as in monotherapy, while using considerably lower doses and thus reducing costs and side-effects. The complementary action of scuPA is especially promising as opposed to the combination of tPA and streptokinase or of tPA and anisoylated plasminogen-streptokinase activator complex. The sequential administration of tPA bolus and a prourokinase infusion to patients with acute myocardial infraction leads to rapid and effective recanalization of coronary vessels with a low reocclusion incidence. The Gusto Angiographic Investigations N. Eng. J. Med 1993, 329: 1615:1622; Cannon CP etal. J Am Coll Cardiol. 1994,24:1602–1610; and Zarich Sw et al. J Am Coll Cardiol 1995, 26:374–379.

The present invention provides regiments for conjunctive thrombolytic therapies using cross-linked covalently bound scuPA/scuPAR and tPA. scuPA/scuPAR and streptokinase. scuPA/suPAR and APSAC. scuPA/suPAR and tcuPA or platelet glycoprotein IIb-IIIa receptor inhibitors. scuPA/suPAR and new thrombolytic derivatives obtained by recombinant DNA technology e.g., E6010, TNK-t-pa, n-PA and others.

Dosage and Formulation

ScuPA/suPAR complexes may be formulated into pharmaceutical preparations for administration to mammals for prevention and treatment of thromboembolic disorders.

Many of the scuPA/suPAR compounds may be provided as protein preparatives with pharmaceutically compatible buffers, including, but not limited to, The therapeutic compounds or pharmaceutical compositions may be administered intravenously, intrapentoneally, locally by catheter, subcutatieously, intramuscularly, intrathecally, orally, rectally, topically or by aerosol.

Formulations suitable for parenteral administration include aqueous and non-aqueous isotonic sterile solutions, which contain buffers, antioxidants and preservatives. The formulations may be in unit dose or multi-close sealed containers.

Patient dosages for intravenous administration of scuPA/suPAR complexes range from about 10 mg to about 100 mg. Dosage amount and interval may be adjusted individually to provide plasma levels of the active moiety which are sufficient to maintain the fibrinolytic activity. A variety of delivery systems for the pharmacological compounds may be employed, including, but not limited to, liposomes and emulsions. The pharmaceutical compositions also may comprise suitable solid or gel phase carriers or excipients. Examples of such carriers or excipients include, but are not limited to, calcium carbonate, calcium phosphate, various sugar, starches, cellulose derivative, gelatin, and polymers such as polyethylene glycols.

Administration of an effective dose of scuPA/suPAR complex alone or in combination with one or more of the above-discussed thrombolytic agents may present or treat thrombolytic disorders in mammals. When another thrombolytic disorders in mammals. When another thrombolytic agent is administered together with a scuPA/suPAR complex, it is administered according to protocols and dosage ranges known to those skilled in the art suitable for such thrombolytic agent.

The present invention is not to be limited in scope by the embodiment disclosed in the example which is intended as an illustration of one aspect of the invention and any methods which are functionally equivalent are within the scope of the invention. Indeed, various modifications of the invention in addition to those shown and described herein will become apparent to those skilled in the art from the foregoing description. Such modifications are intended to fall within the scope of the appended claims.

EXAMPLES

Described below in further detail are chemical synthesis of the covalently bound scuPA/suPAR complex and in vitro studies to show that the activity of the complex in plasma clots alongside the non-cross-linked native scuPA/suPAR. The following materials, methods and studies support and illustrate the invention; they are not intended to be limiting in any way.

Various concentrations of suPAR and its ligand scuPA were incubated in phosphate buffered saline at 4° C. for a period of 1 hour. The preparations were mixed by tilting. Sulfosuccinimidyl suborate ($BS^3$) was added to each preparation to a final concentration of 5 mg/ml and the preparations were incubated at room temperature for an additional 1 hour.

The present invention also contemplates alternate routine chemical procedures used to prepare cross-linked scuPA/suPAR complex by several other chemical methods, for example, by using ultraviolet irradiation or employing other cross-linkers than sulfosuccinimidyl suborate or synthesizing by molecular biology recombinants hybrid molecules that is composed by scuPA and suPAR, are therefore within the scope of the present invention.

The resulting samples were analyzed by two different methods:

(i) To confirm the formation of the cross-linked complex, DTT (50L) was added to 90 OL aliquotes, followed by heating in boiling water for 4 minutes. After addition of glycerol, the reaction sets were run over SDS-PAGE MINI-GEL. The upper gel was 4.5% AAB, and the lower gel 10% AAB. Voltage was fixed to 50 volts. The run time was 1:15 hour. Results of this experiment are described in FIG. 1, which shows the formation of a stable cross linked scuPA-suPAR complex. Lane A shows scuPA alone. Lane B shows scuPA-suPAR complex, as an appearance of a higher molecular weight band that corresponds to the SDS-stable scuPA/suPAR complex.

Figure 2:
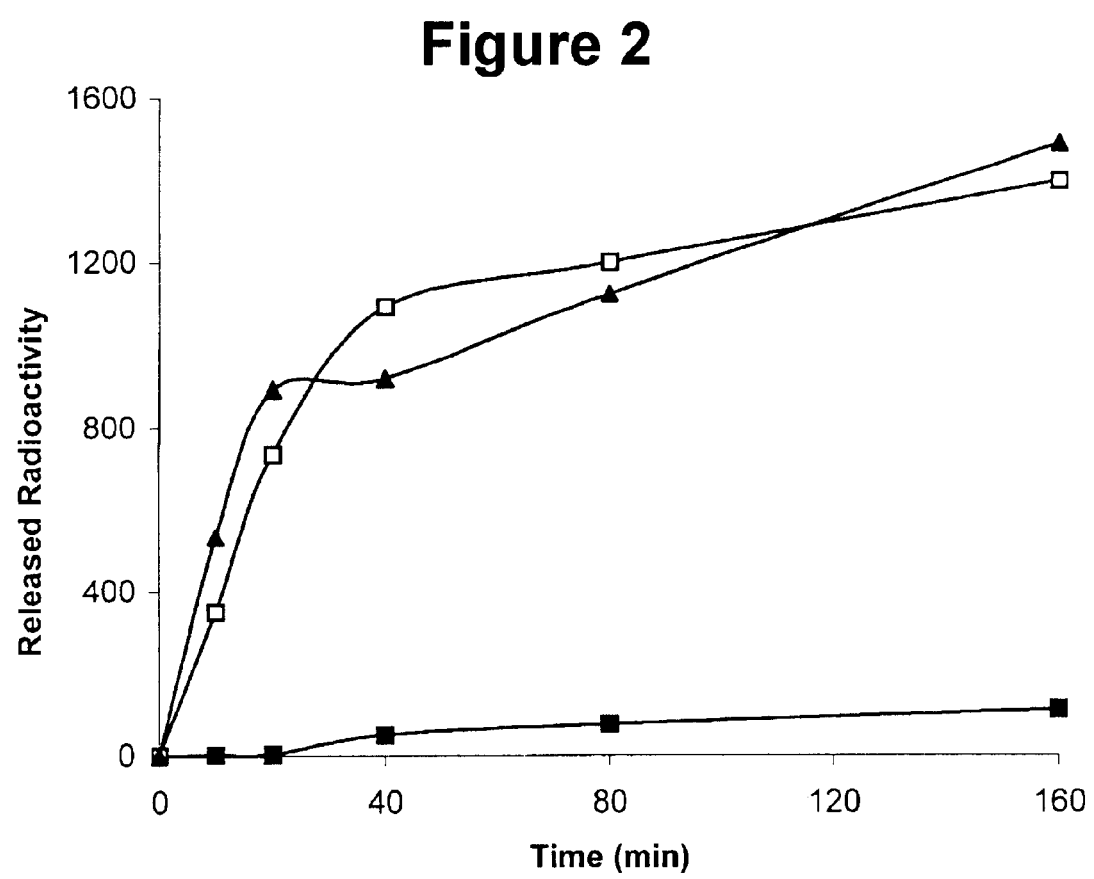
FIG. 2 is a graph depicting the fibrinolytic activity of the cross-linked and/or covalent scuPA-suPAR complex. The capacity of 25 nM of scuPA (filled squares), non-cross-linked scuPA/suPAR or cross-linked scuPA/suPAR complex (triangles) to cleave radio-labeled plasma clots was determined as described below (empty open squares). Released radioactivity indicates that the cross linked and/or covalent complex maintained its fibrinolytic activity in comparison with that of the non-cross-linked scuPA/suPAR complex.

(ii) To confirm that the chemical reaction of binding of scuPA/suPAR did not affect the activity, portions of the reaction mixture were examined using plasma clots as substrate as described in detailed in Blood, 1998, 92:2075–2083. FIG. 2 represents the results which indicate that the fibrinolytic activity of the cross-linked complex was similar to that of the non-cross-linked species. Thus, the covalent binding of scuPA/suPAR provides stability of the scuPA/suPAR complex (which in turn enhances suPA while at the same time does not alter the fibrinolytic activity of the chemically produced suPA/suPAR complex. Since the covalent binding of the single compound suPA/suPAR is irreversible, the use of this complex reduces the effective dosage for optimal fibrinolytic activity, which in turn reduces the side effects caused by high doses. In addition, the decreased dissociation of the crossed linked complex inhibits totally the capacity of isolated scuPA to interact with endogenous urokinase receptor or other receptors present on the endothelial cells thereby decreasing undesired effects such as mutation or vasoactive effects.

Those skilled in the art will recognize, or be able to ascertain using no more than routine experimentation, any equivalents to the specific embodiments of the invention described herein. Such equivalents are intended to be encompassed by the claims.

The present invention is not to be limited in scope by the embodiment disclosed in the example which is intended as an illustration of one aspect of the invention and any methods which are functionally equivalent are within the scope of the invention. Indeed, various modifications of the invention in addition to those shown and described herein will become apparent to those skilled in the art from the foregoing description. Such modifications are intended to fall within the scope of the appended claims.

What is claimed is:

1. A cross-linked urokinase/receptor complex, scuPA/suPAR, comprising a single chain urokinase plasminogen activator (scuPA) covalently bound to a soluble urokinase plasminogen activator receptor (suPAR).

2. A cross-inked urokinase-receptor complex comprising a single chain urokinase plasminogen activator covalently bound to two or more units of soluble urokinase plasminogen activator receptors.

3. The cross-linked scuPA/suPAR complex according to claim 1, said complex having a molecular weight of about 100 kd, and said complex having fibrinolytic activity.

4. The cross-linked scuPA/suPAR complex according to claim 2, said complex having a molecular weight in the range of 100 to 300 kd, and said complex having fibrinolytic activity.

5. The cross-linked scuPA/suPAR complex according to claim 1, further including human IgG, and said combination having fibrinolytic activity.

6. The cross-linked scuPA/suPAR complex according to claim 1, further including tcuPA or tcuPA/suPAR, said combination having fibrinolytic activity.

7. The cross-linked scuPA/suPAR complex according to claim 1, further including a cross-linked urokinase-receptor complex comprising a single chain urokinase plasminogen activator receptors, said combination having fibrinolytic activity.

8. The cross-linked scuPA/suPAR complex according to claim 1, further including tPA, such combination having fibrinolytic activity.

9. The cross-linked scuPA/suPAR according to claim 1, further comprising one or more of the plasminogen activators essentially comprising of tcuPA, tPA, streptokinase, rt-PA, APSC, recombinant scuPA, prourokinase or platelet glycoprotein IIb-IIIa receptor inhibitors.

10. The cross-linked scuPA/suPAR according to claim 2, further comprising one or more of the plasminogen activators essentially comprising of tcuPA, tPA, streptokinase, rt-PA, APSC, recombinant scuPA, prourokinase or platelet glycoprotein IIb-IIIa receptor inhibitors.

11. A cross-linked urokinase/receptor complex, tcuPA/tuPAR, comprising a two chain urokinase plasminogen activator (tcuPA) covalently bound to a suPAR, in equimolar or molar excess of suPAR.

* * * * *